US012758700B2

(12) United States Patent
Adelberger et al.

(10) Patent No.: US 12,758,700 B2
(45) Date of Patent: Oct. 13, 2026

(54) METHOD AND MEANS FOR POSTPRANDIAL BLOOD GLUCOSE LEVEL PREDICTION

(71) Applicant: Roche Diabetes Care, Inc., Indianapolis, IN (US)

(72) Inventors: Daniel Adelberger, Linz (AT); Luigi Del Re, Linz (AT); Florian Reiterer, Vandans (AT); Christian Ringemann, Mannheim (DE); Patrick Schrangl, Linz (AT)

(73) Assignee: Roche Diabetes Care, Inc., Indianapolis, IN (US)

( * ) Notice: Subject to any disclaimer, the term of this patent is extended or adjusted under 35 U.S.C. 154(b) by 472 days.

(21) Appl. No.: 18/486,255

(22) Filed: Oct. 13, 2023

(65) Prior Publication Data

US 2024/0033419 A1 Feb. 1, 2024

Related U.S. Application Data

(63) Continuation of application No. PCT/EP2022/059871, filed on Apr. 13, 2022.

(30) Foreign Application Priority Data

Apr. 14, 2021 (EP) .................................... 21168362

(51) Int. Cl.
*A61M 5/142* (2006.01)
*G16H 10/60* (2018.01)
(Continued)

(52) U.S. Cl.
CPC ............ *A61M 5/142* (2013.01); *G16H 10/60* (2018.01); *G16H 40/60* (2018.01); *G16H 50/30* (2018.01); *A61M 2205/3331* (2013.01)

(58) Field of Classification Search
CPC . A61B 5/7275; A61B 5/14532; A61B 5/4839; A61B 5/7264; A61B 5/7267;
(Continued)

(56) References Cited

U.S. PATENT DOCUMENTS

2007/0020181 A1 1/2007 Workman et al.
2010/0295686 A1 11/2010 Sloan et al.
(Continued)

FOREIGN PATENT DOCUMENTS

RU 2376927 C2 12/2009
WO WO 2020/043922 A1 3/2020

OTHER PUBLICATIONS

International Search Report and Written Opinion for PCT/EP2022/059871, Aug. 5, 2022 (14 pages).
(Continued)

*Primary Examiner* — Jason E Flick
(74) *Attorney, Agent, or Firm* — Bose McKinney & Evans LLP

(57) ABSTRACT

A method for predicting blood glucose levels, in particular, for postprandial blood glucose level prediction, the method being computer-implemented and comprising: receiving a first medical data set of a patient covering a time range, the first medical data set comprising glucose data and further other medical data of the patient, extracting a second medical data set from the first medical data set, wherein the second medical data set is a subset of the first medical data set and wherein the extracting comprises at least one of: identifying duplicates in the first medical data set and removing identified duplicates, identifying data values that lie above a predefined maximum threshold data value or identifying data values that lie below a predefined minimum threshold data value and removing data associated with the identified data values, identifying data values that differ
(Continued)

from predetermined expected data values by more than a predetermined amount and removing data associated with the identified data values, identifying incomplete data for which data values are missing and removing identified incomplete data, identifying at least one predetermined time-dependent data pattern and removing data associated with the identified time-dependent data pattern, providing the extracted second medical data set as input to a blood glucose level prediction model, and predicting future blood glucose levels of the patient using the output of the blood glucose level prediction model based on the second medical data set.

18 Claims, 3 Drawing Sheets

(51) Int. Cl.
*G16H 40/60* (2018.01)
*G16H 50/30* (2018.01)

(58) Field of Classification Search
CPC ....... A61B 5/4848; A61B 5/72; A61B 5/7203; A61B 5/7221; A61B 5/74; A61B 5/742; A61M 2230/201; A61M 5/1723; A61M 2205/50; A61M 5/142; A61M 2005/14296; A61M 2205/3331; G16H 10/60; G16H 50/30; G16H 50/20; G16H 50/50; G16H 50/70; G16H 40/60
See application file for complete search history.

(56) References Cited

U.S. PATENT DOCUMENTS

| | | | |
|---|---|---|---|
| 2012/0246106 A1 | 9/2012 | Atlas et al. | |
| 2016/0354543 A1 | 12/2016 | Cinar et al. | |
| 2018/0353112 A1 | 12/2018 | Dassau et al. | |
| 2019/0290172 A1 | 9/2019 | Hadad et al. | |
| 2020/0196923 A1 | 6/2020 | Kamath et al. | |
| 2020/0205744 A1* | 7/2020 | Patek | A61B 5/7275 |
| 2020/0375549 A1* | 12/2020 | Wexler | A61B 5/14532 |
| 2020/0402634 A1* | 12/2020 | Patek | G16H 50/70 |

OTHER PUBLICATIONS

International Preliminary Report on Patentability for PCT/EP2022/059871, Oct. 12, 2023 (11 pages).

* cited by examiner

METHOD AND MEANS FOR POSTPRANDIAL BLOOD GLUCOSE LEVEL PREDICTION

CROSS REFERENCE TO RELATED APPLICATIONS

This is a continuation of PCT/EP2022/059871 filed Apr. 13, 2022, which claims priority to EP 21168362.8 filed on Apr. 14, 2021, the entire disclosures of both of which are hereby incorporated herein by reference.

BACKGROUND

The present application relates to a method and means for monitoring, controlling and predicting blood glucose levels, in particular for postprandial blood glucose level prediction.

Patients with type 1 diabetes mellitus (T1DM) require insulin injections in order to mitigate the long-term effects of a chronically increased blood glucose (BG) level. However, too much insulin leads to hypoglycemia which is a potentially life threating situation. Managing BG levels by injecting a suitable amount of insulin is a difficult task and a considerable burden for patients with diabetes, especially since there is a large day-to-day variability of BG dynamics and a myriad of factors that influence BG levels. Therefore, the design of smart control algorithms that help patients with managing their BG levels has kept control engineers busy for many years already.

These research efforts have resulted in the design of numerous algorithms for assisting patients with the control of their blood glucose levels, e.g., by warning patients about impeding hypoglycemia or hyperglycemia, by giving insulin dosing advice via a decisions support system, or by providing closed-loop blood glucose control via an artificial pancreas.

Most of these algorithms rely at their core on a mathematical model for the prediction of future BG levels. A whole variety of models has been proposed for this purpose. Typically, these can be categorized either as physiological models or patient-data-based models. Since they are far easier to parametrize/personalize than physiological models, patient data-based models are a focus of current research.

Unfortunately however, models for the prediction of future BG levels, such as physiological models or patient-data-based models, have been found to be able to provide reliable and accurate results for the prediction of future BG levels only under very specially limited and well-controlled circumstances, such as, for example, in clinical settings with a strict regimen of well-defined meal intakes at well-defined times and with well-defined insulin administration dosages at well-defined insulin injection times.

In more practical and realistic settings, i.e., during the daily routine in the real life of a patient outside of any controlled clinical environment or outside of any medical practice environment, it has been found very challenging to obtain robust and reliable predictions or estimates of future BG levels of a patient using the patient-data-based model approach.

SUMMARY

The present application discloses a method and means for obtaining more robust, more accurate and more reliable predictions of future blood glucose levels of a patient. It provides for the ability to identify and obtain more reliable models for describing the overall behavior of the blood glucose levels when using a patient-data-based model or physiological model approach.

In particular, the disclosure provides a method and means for obtaining more robust, more accurate and more reliable predictions of future blood glucose levels of a patient when using a patient-data-based model approach in the case of using medical patient data collected during the daily routine of a patient outside of a controlled clinical setting.

The present disclosure provides the patient with improved means to monitor, manage and control his blood glucose levels based on the obtained output of a patient-data-based model for predicting future blood glucose levels.

The present disclosure includes a computer-implemented method, a computer system, a computer-storage media and a medical device.

For example, a method for predicting future blood glucose levels, in particular for postprandial blood glucose level prediction, can be a computer-implemented method and may comprise one, some or all of the following exemplary possible steps:

- receiving a first medical data set of a patient covering a time range, said first medical data set comprising glucose data and further other medical data of said patient,
- extracting a second medical data set from said first medical data, wherein the second medical data is a subset of the first medical data set and wherein the extracting comprises at least one of:
- identifying duplicates in the first medical data set and removing identified duplicates,
- identifying data values that lie above a predefined maximum threshold data value and removing data associated with said identified data values,
- identifying data values that lie below a predefined minimum threshold data value and removing data associated with said identified data values,
- identifying data values that differ from predetermined expected data values by more than a predetermined amount and removing data associated with said identified data values,
- identifying incomplete data for which data values are missing and removing identified incomplete data,
- identifying at least one predetermined time-dependent data pattern and removing data associated with said identified time-dependent data pattern,
- providing the extracted second medical data set as input to a blood glucose level prediction model or a blood glucose level prediction model algorithm, and
- predicting future blood glucose levels of the patient using the output of the blood glucose level prediction model or blood glucose level prediction model algorithm based on the second medical data set.

Herein, a blood glucose level prediction model may, in particular, be understood as being a patient-data-based blood glucose level prediction model or as a physiological prediction model.

The exemplary glucose data of the first medical data set may originate from a glucose monitoring system that is measuring/recording blood or interstitial fluid glucose values of a patient at regular intervals or at scheduled times.

Herein the term glucose data may be understood as comprising glucose data measured in the interstitial fluid of a patient and/or glucose data measured in the blood of a patient, i.e., blood glucose data. The term glucose level may also be understood as comprising glucose levels of glucose in interstitial fluids and/or glucose levels in blood, i.e., blood glucose levels.

The exemplary step of providing the extracted second medical data set as input to a blood glucose level prediction model may, inter alia, comprise providing the extracted second medical data set as a training data set to a blood glucose level prediction model algorithm, e.g., a neural network algorithm, and training the blood glucose level prediction model algorithm with the extracted second medical data set.

For example, based on the extracted second medical data as a training data set, the blood glucose level prediction model algorithm may be trained to identify the best blood glucose level prediction model and/or to identify the best parameters and/or best parameter values of a blood glucose level prediction model.

Herein, further other medical data may be understood as referring to data on meal intakes, e.g., amount of carbohydrates of/from meal intake(s), data on medication, such as, for example, data on insulin injections or measured or recorded insulin levels, e.g., recorded number/amount of bolus insulin injections or current insulin levels, heart rate, blood pressure, hormonal state/level of a hormone, psychological state, oxygen saturation, other analyte data (i.e. further physiological data other than glucose data/BG, for example, other blood analyte data such as hemoglobin levels) or any other data of medical interest.

Herein the term medical data set covering a time range can, inter alia, be understood as a data set that can be ordered in time such that each data entity or each data type, e.g., blood glucose level or glucose level, can be associated with a point in time, e.g., can be marked with a time stamp.

The medical data set(s) can be in an exemplary electronic format, for example, the first and second medical data set can be structured in a row-based table format, wherein each row or each row index corresponds to a point in time and wherein each row comprises at least one entry for the value of a particular medical data entity or type, e.g., glucose level value or blood glucose level value and wherein each column represents a different or separate data entity or data type, e.g., glucose level or blood glucose level, time, type of meal, amount of carbohydrates of a meal intake, amount of a bolus insulin injection, level of a hormone or other data entities or data types of medical interest.

However, it is also conceivable that the medical data set can also be structured in a column-based format, wherein each column or each column index corresponds to a point in time.

The term data or medical data may, inter alia, be understood as comprising data entities and/or data types and/or data values and/or data points.

The exemplary first medical data set may be a hybrid data set with data automatically retrieved from medical sensors and with data manually inputted by a patient/user.

The term removing data may, inter alia, be understood as removing data from a/said first medical data set including removing the data including any associated data values.

The data format of said possible data entities or data types or data values can, inter alia, comprise numeric types, e.g., floating point types or fixed point types or integer types, string or text types, e.g., character or string, Boolean types, or other types, such as composite types, e.g., arrays, vectors.

Herein the term extracting may also be understood as referring to selecting or generating or filtering and the term identifying may also be understood as referring to checking for or looking for or scanning for.

The exemplary step of identifying duplicates in the first medical data set and removing any identified duplicates, may be understood as comprising the removal of all occurrences of the identified duplicates, i.e., all data related to or associated with the identified duplicates may be removed.

However, it is also possible that one unique occurrence/one unique entry of data of identified duplicates is kept. For example, in case of the occurrence of two identical entries, e.g., two identical rows, in the first medical data set, only one entry/one row is removed from the data set and one entry/one row associated to the identified duplicate(s) is kept.

While it is conceivable that the exemplary first medical data set contains valid multiple identical entries/valid duplicates, e.g., entries having the same data and with the same/identical data values at different times, i.e., at/with different time indices, since, for example, the patient may eat exactly the same meal at different times, suspicious or anomalous double-entries or duplicates may be identified by checking whether such identical entries are recorded as having occurred within a short time interval or even at the same time, e.g., having the same time stamp.

For example, in the case of multiple entries with equal values for the amount of carbohydrates from a meal intake and/or in the case of multiple entries with equal values for the amount of injected insulin, wherein such entries lie within/have been recorded within less than a predetermined short time interval, e.g., within less than 5 minutes in time, said entries may be marked as suspicious or anomalous during an exemplary step of identifying duplicates in the first medical data set and may subsequently be removed from the exemplary first medical data set.

The exemplary step of identifying data values that lie above a predefined maximum threshold data value can be based on a predefined maximum threshold data value derived from statistical analysis of previously recorded medical data sets of the patient.

For example, some data/data values of the first medical data set may indicate unrealistic high amounts of carbohydrate intake(s) and/or unrealistic high amounts insulin inputs.

For example, carbohydrate and bolus insulin intakes with a value bigger/higher than a specific threshold can be marked as suspicious in the data and can be removed from the first medical data.

An exemplary maximum threshold data value, for example, can be calculated/defined as 1.5 times the interquartile range above the 75% quartile (third quartile) of all carbohydrate and/or insulin values of the specific patient, wherein the values may be retrieved from historic patient records.

This specific maximum threshold data value is exemplary only and other ranges/limits and/or other data, e.g., heart rate or other analyte data, can be used to derive maximum threshold data values on which basis data can be removed from the first medical data set.

In other words, a predefined maximum threshold data value can be based on determining the interquartile range above the 75% quartile of all available data values of a specific data type including any previously/historically recorded data values for a patient.

The exemplary step of identifying data values that lie below a predefined minimum threshold data value can also be based on a predefined minimum threshold data value derived from statistical analysis of previously recorded medical data sets of the patient. For example, an exemplary minimum threshold data value can be calculated/defined as 1.5 times the interquartile range below the 25% quartile (first quartile) of all carbohydrate and/or insulin values of the specific patient and requiring that said exemplary minimum threshold data value is not negative, i.e., not less than zero.

Again, said minimum threshold data value is exemplary only and other ranges/limits and/or other data, e.g., heart rate or other analyte data, can be used to derive minimum threshold data values on which basis data can be removed from the first medical data set.

In other words, a predefined minimum threshold data value can be based on determining the interquartile range below the 25% quartile of all available data values of a specific data type including any previously/historically recorded data values for a patient.

It is, inter alia, also possible to set an exemplary predefined minimum threshold data value to be zero, to exclude any negative data/negative data values that may indicate an error in the first medical data set.

The exemplary step of identifying data values that differ from predetermined expected data values by more than a predetermined amount and removing data associated with said identified data values, may, for example, comprise checking for unrealistic/suspicious carbohydrate to insulin ratios.

For example, a base for such a check for unrealistic/suspicious carbohydrate to insulin ratios can be an estimate for the expected injected bolus insulin amount, $BI_{expected}$, which can be computed according to the following formula:

$$BI_{expected} = \frac{CHO}{CIR} + \frac{\Delta G}{ISF} \quad (1)$$

Herein CHO is the carbohydrate content of a meal or amount of carbohydrates of a meal intake, ΔG is the deviation of the glucose value or blood glucose value, $BG_{CGM}$, measured/recorded by a glucose monitoring system, e.g., by a continuous glucose monitoring system (CGM), from a nominal target glucose value or blood glucose value, $BG_{target}$, e.g. $BG_{target}$ set to 110 mg/dl, i.e. $\Delta G = BG_{CGM} - BG_{target}$.

For example, identifying data values that differ from predetermined expected data values by more than a predetermined amount may comprise checking whether a recorded bolus insulin amount differs from an expected bolus insulin amount by more than a predetermined amount, e.g., by more than 10, 20 or 40%.

Herein, the term continuous glucose monitoring system (CGM) can be understood as referring to a glucose monitoring system that is measuring/recording glucose values, e.g., blood glucose values and/or interstitial glucose values, of a patient at regular intervals or at scheduled times, wherein the frequency with which glucose levels of a patient can be measured/recorded can be up to 12 measurements per hour, i.e., with a sampling time $T_s$ of 5 minutes, or the frequency can be higher, e.g., every minute or even with sampling times of less than a minute.

These measurements may, for example, be taken by a transcutaneous sensor that is implanted in a patient as part of the glucose monitoring system.

Furthermore, CIR is a patient specific carbohydrate-to-insulin-ratio value or factor that, for example, has been set by the patient himself or with the assistance of a medical doctor and ISF is a patient specific insulin sensitivity factor that also may, for example, have been set by the patient himself or with the assistance of a medical doctor.

A patient may rely on said CIR and ISF values to compute their specific bolus insulin injection needs.

The above exemplary defined expected bolus insulin amount $BI_{expected}$ depends on the two ratios CHO/CIR and ΔG/ISF. Anomalous deviations in either one of the ratios can be reflected in a measured/recorded injected bolus insulin amount, BI, value.

With the above identified exemplary parameters, data or data points or data subsets or data segments of the first medical data set can be identified/marked as suspicious/anomalous when the measured/recorded BI-value differs from a predetermined expected injected bolus insulin amount or value by more than a predetermined amount or value.

For example, one could mark data or data points or data subsets or data segments of the first medical data set for removal when the measured/recorded BI-value differs by more than 10, 20 or 40% from the expected value $BI_{expected}$.

For example, one could check if a measured/recorded BI-value of the first medical data set is outside the following bounds:

$$l \cdot BI_{expected} < BI < u \cdot BI_{expected} \quad (2)$$

With l being a factor for setting the lower bound and with u being a factor for setting the upper bound and with l<u. Exemplary, l may be set to 0.6 and u may be set to 1.4 when requiring that data with a measured/recorded BI-value that differ by more than 40% from the expected value $BI_{expected}$ should be removed from the first medical data set.

The step of identifying incomplete data for which data values are missing and removing identified incomplete data from the first medical data set, may, inter alia, comprise checking for a missing time/missing time stamp of data and/or checking for a wrong data format, e.g., the occurrence of a string of characters instead of an expected float or integer value and/or may comprise checking for a missing data value for an expected data entity or data type.

The step of identifying at least one predetermined time-dependent data pattern and removing data associated with said identified time-dependent data pattern, may, for example, comprise checking for any unexplainable or invalid rises or falls in certain data values over time.

In other words unexpected or unexplainable or invalid rises or falls in certain data values over time may be considered as predetermined time-dependent data patterns or as anomalous temporal signatures in a subset of the first medical data set.

For example, identifying/detecting an invalid rise in glucose levels or blood glucose levels in data from a glucose monitoring system/device, such as, for example, data recorded/measured by a continuous glucose monitoring system/device, CGM, that cannot be associated with a meal intake (which itself also can be an indication of an incomplete data set/incomplete data entry) can be detected/identified using the following exemplary computer-implementable method and criteria:

Filtering the first medical data set, in particular the data on glucose levels or blood glucose levels, e.g., time-dependent data from a/the glucose monitoring system/device, using a filter, e.g., using a Savitzky-Golay-Filter (SGF) with filter parameters d and w, wherein the filter parameter d refers to a/the polynomial degree and wherein the filter parameter w refers to a/the window size of the Savitzky-Golay-Filter.

Thereby a filtered time signal y(t) of glucose levels or blood glucose levels can be obtained.

Detecting all minima and maxima in the filtered signal y(t).

For each rising segment in the filtered signal y(t), e.g., for each minimum until the next maximum in filtered signal y(t), the following steps can be carried out:

a) Identifying the following points in time $t_{min}$: time where a local minimum occurs in y(t)

$t_{max}$: time where the next local maximum occurs in y(t) after $t_{min}$ $t_1$: time where $\dot{y}(t)$, the first derivate of y(t), has the largest value in the interval $[t_{min}, t_{max}]$ $t_2$: time where $\ddot{y}(t)$, the second derivate of y(t), has the largest value in the interval $[t_{min}, t_{max}]$ $t_{start}=t_{min}-\Delta T$, wherein $\Delta T$ is a time shift $t_{end}=t_2+\Delta T$ b) Determining $\Delta y=y(t_{max})-y(t_{min})$, the difference in glucose levels/blood glucose levels between the time of a local maximum and the time of a local minimum.

c) Determining if the following condition $$\Delta y > \Delta y_{min} \wedge \dot{y}(t_1) > \dot{y}_{min} \wedge \sum_{t=t_{start}}^{t_{end}} c(t) \leq c_{min} \tag{3}$$

is satisfied, wherein c(t) denotes the corresponding data values for the amount of carbohydrates from meal intakes at a given time, i.e., denotes a time-dependent carbohydrates input signal, $\Delta y_{min}$ denotes a threshold for a minimum rise in glucose levels/blood glucose levels and wherein $\ddot{y}_{min}$ denotes a rate-of-change threshold for the change in glucose levels/blood glucose levels.

If said condition is satisfied, then the time interval $[t_{min}, t_{max}]$ can be considered an invalid rise in glucose levels or blood glucose (BG) levels and data or data segments associated with that invalid rise can be marked as suspicious and can be removed from the first medical data set.

Exemplary parameters and exemplary parameter values for the above exemplary described possible steps of using a Savitzky-Golay-Filter (SGF) to identify a predetermined time-dependent data pattern such as an anomalous or suspicious or invalid rise in glucose levels/blood glucose (BG) levels are listed in the following table I.

TABLE I

PARAMETERS OF ALGORITHM TO DETECT GLUCOSE/BG RISES W/O MEAL INPUT

| Parameter | Symbol | Unit | Value |
|---|---|---|---|
| SGF degree | d | 1 | 3 |
| Window size of SGF | w | min | 120 |
| Rate-of-change threshold | $\dot{y}_{min}$ | mg/dl/min | 0.75 |
| Threshold for min. glucose/BG rise | $\Delta y_{min}$ | mg/dl | 30 |
| Time shift | $\Delta T$ | min | 30 |
| Min. amount of carbs | $C_{min}$ | g | 0 |

Besides the above exemplary described set of rules and criteria to detect incomplete or erroneous or invalid data or data points or data segments, additionally, a check can be implemented to identify data or data points or data segments in the first medical data set or in the second medical data set that are particularly well suited as starting points or data segments to be inputted to a blood glucose level prediction model in order to facilitate identifying/determining the best blood glucose level prediction model parameters/parameter values.

For example, a suitable valid starting point in the first medical data set or in the second medical data set might be identified as a meal intake of a predetermined minimum amount of carbohydrates, e.g., of at least 20 g of carbohydrates, with a simultaneous injection of an appropriate amount of bolus insulin, e.g., an amount of bolus insulin that is not marked as invalid or suspicious and that is, for example, in agreement with expected injection amounts of bolus insulin, as described further above.

A suitable data segment on whose basis best-fit model parameter values of parameters of a blood glucose level prediction model can be derived from may be defined by commencing with a valid starting point and ending with a data point that is marked as suspicious or with a last data point before a hole or a gap in the first medical data set, for example, a gap longer than a predetermined duration, e.g., longer than 30 minutes. In case the segment ends with a data point that is marked as suspicious that data point can be removed and the last data point before said suspicious data point can be used to mark the end of a data segment.

In addition, or alternatively, the end of a valid data segment may be defined by identifying a marker for a next valid starting point or the end of a valid data segment can be defined by the lapse of a predetermined time duration after the beginning of the data segment, e.g., 2 hours after the first point of the data segment, whichever may occur first.

To further facilitate the use of data segments of the first medical data set or of the second medical data set for identifying the best blood glucose level prediction model parameters/parameter values, a minimum length/a minimum duration can be set for the identification/selection of data segments of the first medical data.

For example, the step of providing the extracted second medical data set as input to a blood glucose level prediction model data may comprise identifying in the second medical data set at least one data segment, wherein a data segment is a subset of a plurality of data points of the extracted second medical data set that covers at least a minimum time range.

For example, it can be defined/required that a data segment has to be at least 30 minutes long.

The above-mentioned exemplary second medical data set may be derived from the first medical data set by removing data from the first medical data set according to any of the above exemplary described methods, criteria or rules.

In addition or alternatively, the above-mentioned exemplary second medical data set may be derived from/generated from the first medical data set by extracting valid data segments from the first medical data set according to any of the above exemplary described methods, criteria or rules.

Furthermore, once a second medical data set has been derived from said first medical data set, the second medical data set can be split up according to a predefined schedule, such as for example, splitting the second medical data set into three different parts that are associated to meal times such as breakfast, lunch and dinner times.

Following such an exemplary division of the second medical data set into different parts, each part of the second medical data set can be provided as separate input to a blood glucose level prediction model to derive model parameters for each different part, thereby better reflecting the effect of the meal times on the prediction performance of the model to predict future blood glucose levels.

For example, separate model parameter sets can be identified for breakfast, lunch and dinner time. Breakfast models can, for example, be identified from data segments with a starting point between 5:30 a.m. and 10:30 a.m., lunch models from those with a starting time between 10:30 a.m. and 2:30 p.m., and dinner models from those with a starting time between 5:00 p.m. and 9:00 p.m.

However, such a splitting of the second medical data into different parts and the separate modelling of the parts is optional.

Internal trials and tests have unexpectedly and surprisingly found that when pre-processing a first medical data set according to any of the above exemplary described methods, criteria or rules to derive a second medical data set, which is a subset of the first medical data set, and using said derived second medical data set as input to a blood glucose level prediction model for predicting future blood glucose levels of a patient, in particular, for the postprandial blood glucose level prediction of a patient, the robustness, performance, reliability and accuracy of the prediction of future blood glucose levels is improved to unprecedented quality levels.

This further advantageously enables the provision of more accurate and more relevant warnings to patients with respect to critical blood glucose levels and enables the provision of more accurate recommendations for administering appropriate dosages of insulin, on whose basis, for example, insulin pumps can be controlled.

Furthermore, it has been found that when pre-processing a first medical data set according to any of the above exemplary described methods, criteria or rules to derive a second medical data set, which is a subset of the first medical data set, said second medical data set facilitates significantly the identification of the best blood glucose level prediction model and the identification of its best model parameters. Being able to easier identify the best blood glucose level prediction model(s) not only improves the results for predicting future glucose levels of a patient, but also improves the results for modelling the overall behavior or overall trajectory of the evolution of glucose levels of a patient.

To further aid in some technical aspects of the present disclosure, a possible exemplary blood glucose level prediction model is described below which can be used to predict future blood glucose levels of patient on the basis of the above-described second medical data set.

For example, a suitable patient-data-based blood glucose level prediction model is the Kirchsteiger model (denoted with PM1) that describes the blood glucose response to carbohydrate intakes, as well as to bolus insulin injections, and that can be expressed with the following formula:

$$BG_{CGM}(s) = \frac{K_1}{(1+sT_1)^2 s} \cdot D(s) + \frac{K_2}{(1+sT_2)^2 s} \cdot U(s) \tag{4}$$

In this formula, $BG_{CGM}(s)$, which also can be denoted with CGM(s), describes the glucose level(s)/blood glucose level (s) measured/recorded via a continuous glucose monitoring (CGM) system, D(s) the carbohydrates of meal intakes and U(s) the bolus insulin injections, all in the Laplace domain parametrized by the complex frequency s, wherein, the transformation from the time domain t into the Laplace domain s can be described by the following Laplace transformation $$F(s) = \int_o^{\infty} f(t)e^{-st}dt.$$

Other influencing inputs like basal insulin, stress, sports, mixed meal composition, etc. are not incorporated into this model structure.

The parameters in equation (4) have an easy to grasp physiological interpretation: Whereas $K_1$ describes the effect of 1 gram of carbohydrates on glucose levels, $K_2$ corresponds to the effect of 1 IU of bolus insulin (both for time $t \rightarrow \infty$). Time constants $T_1$ and $T_2$ are proportional to the response time to carbohydrate and insulin inputs.

In the Kirchsteiger model according to equation (4), carbohydrate and insulin inputs are assumed to have a persistent effect on glucose levels, which is caused by the fact that both transfer functions contain an integrator term (pole at s=0). Such a behavior is strictly speaking not physiological, but has some parallels with the simple heuristics of Advanced Carbohydrate Counting (ACC) used for calculating meal bolus insulin needs. Parameter $K_2$ has the same interpretation as the insulin sensitivity factor ISF, whereas the ratio $K_2/K_1$ tells how many grams of carbs are compensated by 1 IU, just as it is the case for the carbohydrate-to-insulin ratio CIR in ACC.

To identify the best-fit model parameters/parameter values of a chosen patient-data-based blood glucose level prediction model, such as the Kirchsteiger model described above, the second medical data set can be inputted in said patient-data-based blood glucose level prediction model and the best-fit model parameters/parameter values can be determined by minimizing a cost function.

A possible suitable exemplary cost function to optimize/minimize in order to determine the best-fit model parameters of a blood glucose level prediction model, such as the above described Kirchsteiger model, is the following exemplary cost function J(θ):

$$J(\theta) = \sum_{d=1}^{d_{tot}} \left( \sum_{k=k_0(d)}^{k_N(d)} f(y_k, \hat{y}_k(\theta))^2 \right) \tag{5}$$

with $$f(y_k, \hat{y}_k(\theta)) = \begin{cases} y_k - \hat{y}_k(\theta) & \text{if } y_k < 100 \text{ mg}/dl \\ 100 \cdot \dfrac{y_k - \hat{y}_k(\theta)}{y_k} & \text{if } y_k \geq 100 \text{ mg}/dl \end{cases} \tag{6}$$

In this cost function, $y_k$ corresponds to the measured output of a glucose monitoring system such as a continuous glucose monitoring system, i.e., $y_k$ corresponds to the glucose data/blood glucose level data/blood glucose values $BG_{CGM}$ and $\hat{y}_k$ denotes the output of the chosen blood glucose level prediction model, e.g., the Kirchsteiger model.

Furthermore, d denotes a data segment, for example, a data segment from the second medical data set that was identified from a first medical data set as described above. Stated differently, a data segment can be understood as a subset of the first medical data set, wherein the data of the data segment have been extracted/selected/filtered from the first medical data set according to one or more criteria and/or rules described above.

The total number of data segments is denoted with $d_{tot}$, i.e., there are 1 . . . $d_{tot}$ data segments. For easier readability of the expression of the cost function, the index for the data segments has been intentionally omitted in the above-described definition of the cost function J(θ). However, it is to be understood that d can have its own index, e.g., $d_m$, with m=1, . . . $d_{tot}$.

Each data segment d can further be characterized by a starting index $k_0$ and an end index $k_N$, i.e., the index k can be used to index individual data points/individual data within a given data segment d.

The vector $\theta$ describes the model parameters, i.e., in the exemplary case of the Kirchsteiger model, said model vector $\theta$ may depend on the parameters $K_1$, $K_2$, $T_1$ and $T_2$.

The model output $\hat{y}_k$ can be computed using the model parameters $\theta$ and an estimate of the initial state $\hat{x}_0$.

This initial state estimate may correspond to the state of the model at the start $k_0$ of a data segment and may correspond to the best estimate of the glucose level value at the start of a data segment. Said initial state estimate can be estimated/derived/determined for each data segment.

As will be exemplary described further below, said initial state estimate may, for example, be derived by using a Kalman filter and/or by using an autoregressive approach.

For each data segment of a patient the same model parameter vector $\theta$ can be used.

The minimization of this exemplary cost function can be, inter alia, performed using either a brute-force search algorithm over a grid of model parameter vector $\theta$ values or can be performed by local gradient search algorithms, e.g., a simplex algorithm, or by global optimization algorithms, e.g., genetic algorithms, simulated annealing algorithms, Markov chain Monte Carlo algorithms or other techniques.

The derived best-fit model parameters $\theta_{best}$ may then be used to predict future blood glucose levels of the patient, in particular, to predict postprandial blood glucose levels of the patient.

In particular, the derived best-fit model parameters $\theta_{best}$ may then, for example, be used together with further information from data from the second medical data set, such as meal size and/or injected bolus quantity to simulate the postprandial future glucose trajectory of a patient.

As indicated above, it has been found that using a blood glucose level prediction model such as the one exemplary described above on a medical data set, i.e., on a second medical data set described above, that was extracted/selected/generated from a first medical data set as described above, yields unprecedented robust, reliable and accurate predictions of future blood glucose levels of a patient that are superior to any current known prediction techniques.

Optionally, the application of the above-described blood glucose level prediction model may be further refined by using a Kalman filter to estimate an initial state of the model.

For example, a Kalman filter can be used to estimate the state of the model before the starting point of a (first) data segment, e.g., 6 hours before the starting point of a (first) data segment, and to compute estimates for the state for each of those time points up to the start of a first data segment d.

The last estimate of $\hat{x}$ (just at the start of the identification data segment) may then correspond to the initial state $\hat{x}_0$ of the blood glucose level prediction model.

The model inside the Kalman filter (derived from the model with parameters $\theta$) can be updated in every iteration step of the optimization using the latest estimate of the model parameters $\theta$, i.e., the model used for the prediction and the (same) model used inside the Kalman filter can be optimized simultaneously.

A new Kalman filter can be instantiated and applied in each iteration step and can be used to compute the state estimates $\hat{x}(t_{k_0})$ at each time $t_{k_0}$ based on input (d, u) and output ($\Delta y = y - G_b$) data up to time $t_{k_0}$, wherein $G_b$ can be an estimate of the patient's basal glucose level, wherein u is the input in the time domain.

Using the estimated state $\hat{x}(t_{k_0})$ at time $t_{k_0}$ as initial condition, a simulation with the process model k steps into the future can be computed ($y_{sim,k}(t_{k_0})$).

A prediction for time $t_{k_0}+kT_S$ (with $T_S$ being the sampling time) can thus, for example, be calculated as:

$$\hat{y}(t_{k_0}+kT_S|t_{k_0}) = y_{sim,k}(t_{k_0}) + G_b \quad (7)$$

The combination of the exemplary Kirchsteiger model (PM1) and the exemplary Kalman filter (KF) may also be referred to as KF-PM1.

In the case of not using a Kalman filter, i.e., in the case of just using the basic Kirchsteiger model (PM1), said equation (8) may also be used for a prediction of future glucose levels by setting the estimated state $\hat{x}(t_{k_0})$ at time $t_{k_0}$ to zero.

Alternatively, a hybrid approach may be adopted, wherein the initial state $\hat{x}_0$ may be assumed to be zero for the model (i.e., no impact of the initial state on the model output), but the effect of the initial state may be captured by an autoregressive (AR) model instead.

The predicted glucose output of this exemplary hybrid model approach may correspond to the sum of the chosen blood glucose level prediction model prediction(s) and the prediction(s) by the AR model.

A population mean AR model with parameter values identified from data during the night period (i.e., without any influence of meals) may be used for this purpose.

Let $\hat{y}_{AR}(t_{k_0}+kT_s|t_{k_0})$ be the prediction of time $t_{k_0}+kT_s$ given information from up to time $t_{k_0}$.

The combined model output for the predicted glucose trajectory may then be calculated according to the following equation:

$$\hat{y}(t_{k_0}+kT_S|t_{k_0}) = y_{sim,k}(t_{k_0}) + \hat{y}_{AR}(t_{k_0}+kT_S|t_{k_0}) \quad (9)$$

where $y_{sim,k}(t_{k_0})$ is the output of the blood glucose level prediction model simulated with the assumption of $\hat{x}_0 = x(t_{k_0}) = 0$ as initial condition.

The combination of the exemplary Kirchsteiger model (PM1) and the exemplary autoregressive model (AR) may also be referred to as the AR-PM1 approach.

While a blood glucose level prediction model based on the Kirchsteiger model when used on the second medical data set already provides very satisfying performance results, it is also possible, as previously indicated, that the second medical data set may be provided as input also to other blood glucose level prediction models, not only to the exemplary models PM1 or its variants, KF-PM1 or AR-PM1.

Furthermore, in addition or alternatively to the above-described steps to identify the best model and/or best model parameter and/or best model parameter values, it is also possible to use a neural network algorithm or a similar algorithm that was trained on an exemplary extracted second medical data in order to identify the best blood glucose level prediction model and/or the best model parameters and/or best model parameter values.

For completeness, the following further possible examples for other blood glucose level prediction models that can be used are exemplary described in the following. It is also possible to feed the second medical data set to a plurality of different blood glucose level prediction models at the same time in order to compare, gauge and calibrate their relative performances.

Zero Order Hold: The zero order hold (ZOH) model computes the prediction $\hat{y}$ at time $t+kT_s$ based on the $BG_{CGM}$ data y up to time t by keeping the latest available value constant, i.e., $$\hat{y}(t+kT_s) = y(t) \quad (10)$$

Global AR Model: A simple, second order global autoregressive AR model of the form $$\Delta\hat{y}_{AR}(t+kT_s) = a_k\Delta y(t) + b_k\Delta y(t-T_S) \quad (11)$$

$$\Delta y(t)=y(t)-G_b \quad (12)$$

$$\hat{y}_{AR}(t+kT_s)=\Delta\hat{y}_{AR}(t+kT_s)+G_b \quad (13)$$

can be used (where $G_b$ is again the patient-specific estimate of the basal glucose level). The parameters ($a_k$, $b_k$) are optimized using least squares (LS) optimization for each prediction horizon k.

It should be noted that even though the structure of the global AR model used for this purpose can be identical to that inside the hybrid AR-PM1 approach described above, the model parameters may differ.

Whereas the AR model inside the AR-PM1 context is identified only from data during the night, the global AR model used as a baseline can be based on data from the entire 24-hour period of each day.

Alternative Model Structure: To put the prediction performance of the PM1 model into context, additionally, an alternative model structure without integrator terms is analyzed:

$$BG_{CGM}(s)=\frac{K_1}{(1+sT_1)^2}\cdot D(s)+\frac{K_2}{(1+sT_2)^2}\cdot U(s) \quad (14)$$

This alternative model may be referred to as PM2 and may be also implemented using a Kalman filter or with using an autoregressive (AR) model in which case said variants may be referred to as KF-PM2 or AR-PM2.

No matter which blood glucose level prediction model is chosen to obtain future blood glucose levels of a patient based on the second medical data set, an obtained prediction of future blood glucose levels can be displayed to a patient, for example on a display of a glucose monitoring system or on the display of a computing device, e.g., a smartphone or personal computer.

Furthermore, it is possible that based on an obtained prediction of future blood glucose levels, a recommended dosage of insulin to be administered is displayed to a patient.

In addition, it is possible that based on an obtained prediction of future blood glucose levels, a recommended dosage of insulin is automatically administered via automatic control of an insulin pump.

In other words, the present disclosure facilitates the monitoring, predicting and controlling of blood glucose levels of a patient and also facilitates the control of administering appropriate dosages of insulin in a reliable and accurate manner.

All of the herein described method steps for predicting blood glucose levels are computer-implementable, i.e., they can for example be executed by a computing system comprising a computer memory, one or more processors and optionally a display.

A computing system can, for example, be one of the following types: a computer server, a personal computer or a mobile computing system, e.g., a smartphone, tablet or laptop.

Furthermore, the present invention can be implemented as a glucose monitoring system comprising a sensor for obtaining glucose data/blood glucose data of a patient, a computer memory, one or more processors and a display, wherein the computer memory of the glucose monitoring system may comprise computer-executable instructions which, when executed by the one or more processors of the glucose monitoring system, cause the one or more processors to perform one, some or all of the herein described steps for predicting blood glucose levels.

The exemplary glucose monitoring system may further comprise an insulin pump and the glucose monitoring system can further be configured to control the insulin pump, in particular for controlling the dosage of insulin that can be administered by the insulin pump.

The exemplary glucose monitoring system may also be configured to determine a recommended dosage of insulin to be administered based on an obtained prediction of future blood glucose levels.

Furthermore, the above and in the following described computer-implementable method steps may be stored on one or more computer-storage media, e.g., non-volatile computer-storage media, storing computer-executable instructions that, when executed by a computer system, can perform a method according to either one, some or all of the above and in the following exemplary described method steps for predicting blood glucose levels.

BRIEF DESCRIPTION OF THE DRAWINGS

The above mentioned and other features of this disclosure, and the manner of attaining them, will become more apparent and the disclosure itself will be better understood by reference to the following description of embodiments of the invention taken in conjunction with the accompanying drawings, wherein the following figures merely serve to illustrate the following technical aspects.

Figure 1:
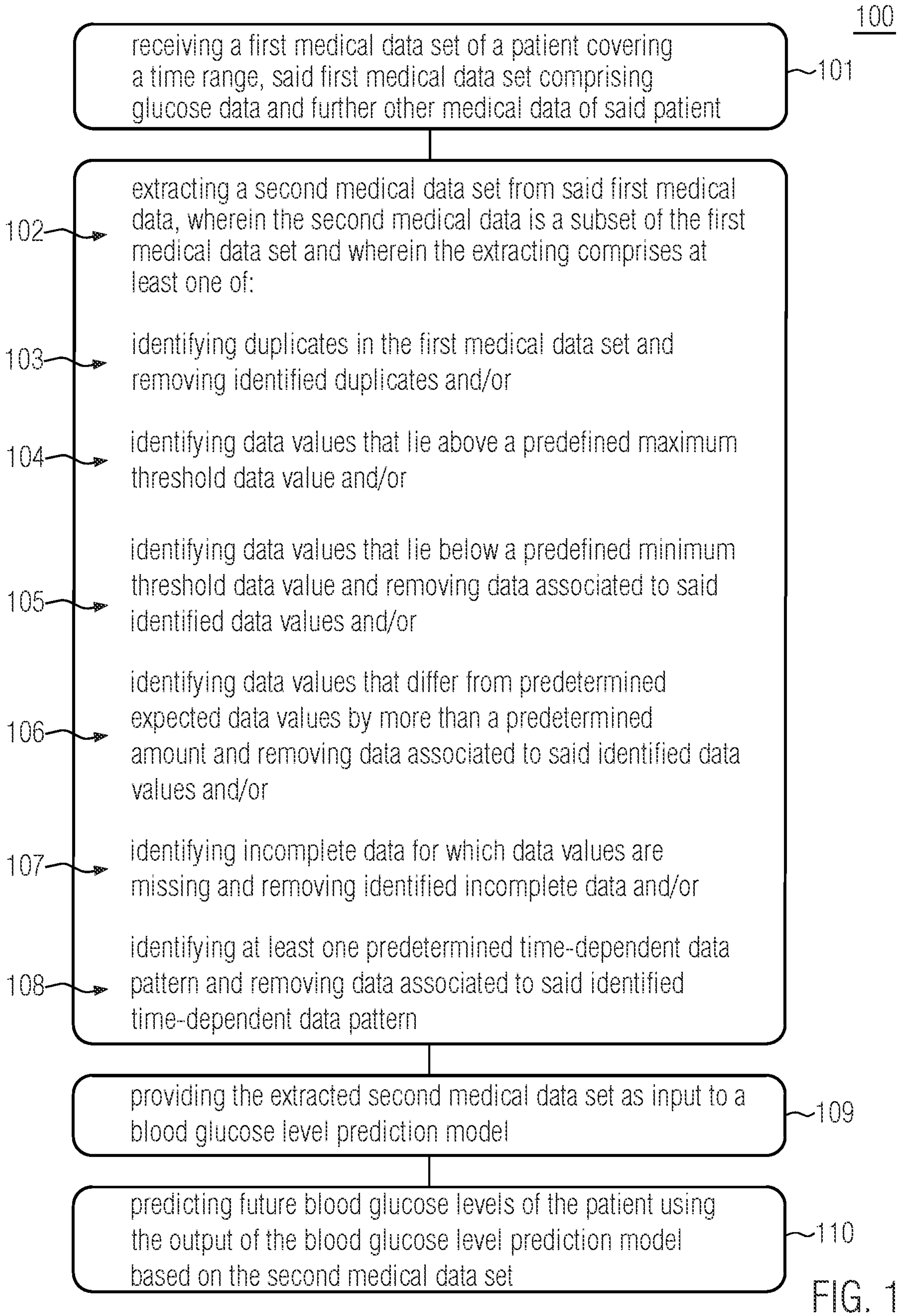
FIG. 1 is an exemplary flow diagram for predicting blood glucose levels.

Corresponding reference characters indicate corresponding parts throughout the several views. Although the exemplification set out herein illustrates embodiments of the invention, in several forms, the embodiments disclosed herein are not intended to be exhaustive or to be construed as limiting the scope of the invention to the precise forms disclosed.

DETAILED DESCRIPTION

FIG. 1 schematically shows exemplary possible steps of a computer-implementable method, 100, for predicting blood glucose levels, in particular, for postprandial blood glucose level prediction. Therein, an exemplary first medical data set of a patient covering a time range can be retrieved or received, 101, for processing. The exemplary first medical data set includes blood glucose data and further, other medical data of the patient.

For example, the blood glucose data may originate from/may be received from/may be retrieved from a sensor of a glucose monitoring system and the other medical data may comprise at least one of the following: data on meal intakes, e.g., amount of carbohydrates from meal intakes, or data on medication, e.g., data on insulin injections or measured insulin levels, and/or other analyte data, wherein the exemplary other analyte data or insulin data may also originate from a medical sensor.

Alternatively, or in addition, a patient can himself input data, e.g., data on meal intakes, e.g., amount of carbohydrates from meal intakes, or data on medication, blood glucose levels or insulin levels.

In other words, the first medical data set may be a hybrid data set with data automatically retrieved from medical sensors and with data manually inputted by a patient/user.

In order to generate a second medical data set, the exemplary second medical data set may be extracted, 102, from the exemplary first medical data set on the basis of at least one of the following rules or criteria:

identifying, 103, duplicates in the first medical data set and removing identified duplicates, and/or identifying, 104, data values that lie above a predefined maximum threshold data value, or identifying, 105, data values that lie below a predefined minimum threshold data value and removing data associated to said identified data values, and/or identifying, 106, data values that differ from predetermined expected data values by more than a predetermined amount and removing data associated to said identified data values, and/or identifying, 107, incomplete data for which data values are missing and removing identified incomplete data, and/or identifying, 108, at least one predetermined time-dependent data pattern and removing data associated to said identified time-dependent data pattern.

The exemplary second medical data set generated/extracted from the first medical data set can then automatically be fed into/provided to/inputted, 109, to a blood glucose level prediction model.

Any of the above described or other blood glucose level prediction models can be used with the extracted second medical data set.

Based on the output of the blood glucose level prediction model on the basis of the second medical data set, future blood glucose levels of the patient, in particular, postprandial blood glucose levels of the patient, can be predicted, 110, with unprecedented accuracy and robustness.

Figure 2:
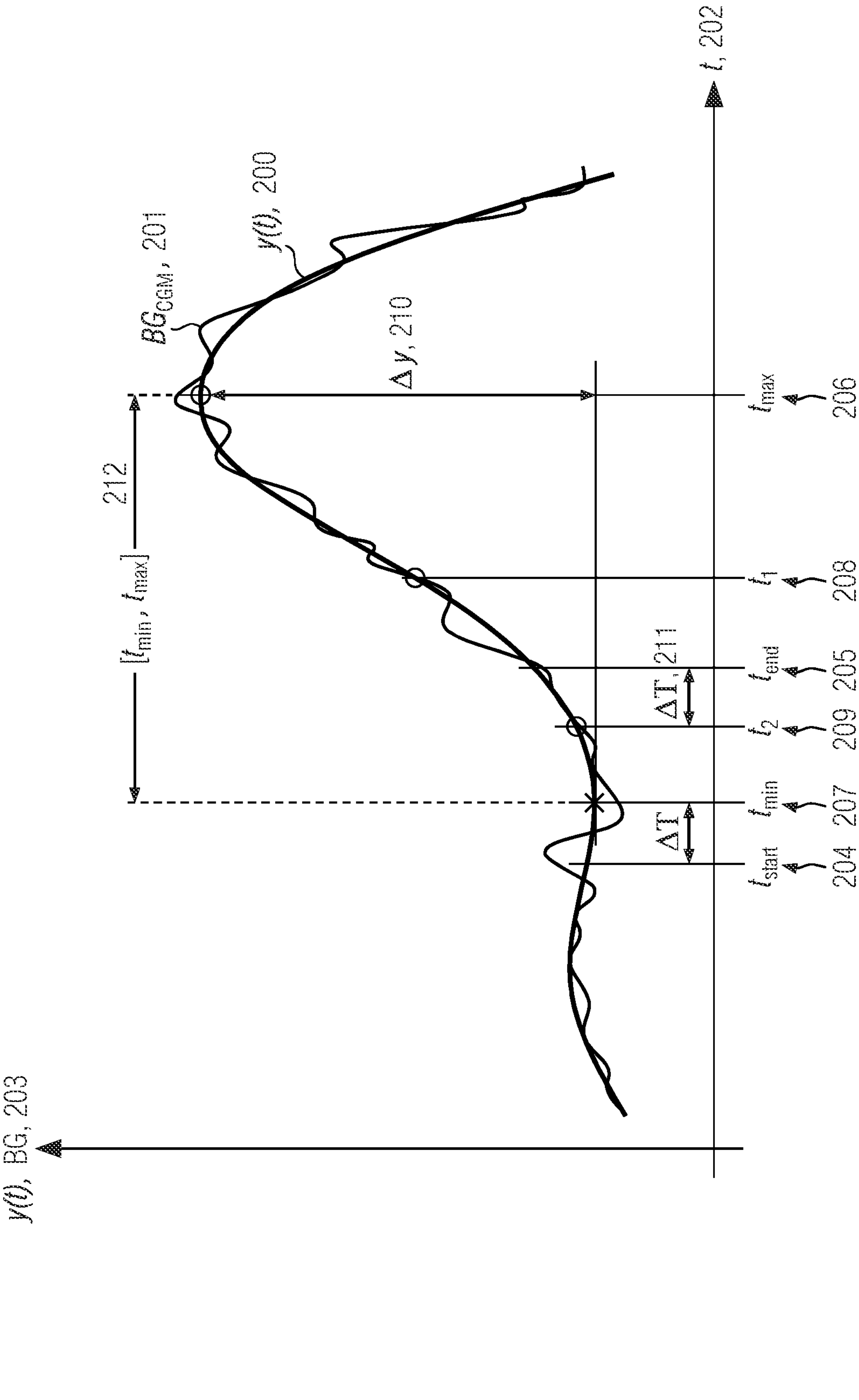
FIG. 2 is a view of exemplary filtered blood glucose data/exemplary filtered glucose data.

FIG. 2 schematically shows an exemplary filtered blood glucose data signal y(t), 200, that was obtained from filtering data 201 on (raw, unfiltered) blood glucose levels, e.g., time-dependent data $BG_{CGM}(t)$ from a glucose monitoring system, using a filter, e.g., using a Savitzky-Golay-Filter (SGF) as described above and with the exemplary parameters of table I.

Therein, the reference numeral 203 marks the ordinate axis of exemplary glucose values or blood glucose values, BG, and the reference numeral 202 marks the abscissa axis of exemplary time t.

As described earlier, an exemplary identifying/detecting of an invalid rise in blood glucose levels in data from a glucose monitoring system, such as for example, data recorded/measured by a continuous glucose monitoring system, CGM, that cannot be associated to a meal intake (which itself also can be an indication of an incomplete data set/incomplete data entry) can be detected/identified using the following exemplary computer-implementable method and criteria:

Detecting all minima and maxima in the filtered signal y(t), 200. Here the exemplary depicted signal 200 has two maxima and one minimum.

For each rising segment in the filtered signal y(t), e.g., for each minimum until the next maximum in filtered signal y(t), the following steps can be carried out:

a) Identifying the following points in time $t_{min}$: time, 207, where a local minimum occurs in y(t)

$t_{max}$: time, 206, where the next local maximum occurs in y(t) after $t_{min}$ $t_1$: time, 208, where $\dot{y}(t)$, the first derivate of y(t), has the largest value in the interval $[t_{min}, t_{max}]$ $t_2$: time, 209, where $\ddot{y}(t)$, the second derivate of y(t), has the largest value in the interval $[t_{min}, t_{max}]$ $t_{start}$, 204: $t_{start}=t_{min}-\Delta T$, wherein ΔT, 211, is a time shift $t_{end}$, 205, $t_{end}=t_2+\Delta T$ b) Determining Δy, 210: $\Delta y=y(t_{max})-y(t_{min})$, the difference in glucose levels/blood glucose levels between the time of a local maximum and the time of a local minimum.

c) Determining if the following condition $$\Delta y > \Delta y_{min} \wedge \dot{y}(t_1) > \dot{y}_{min} \wedge \sum_{t=t_{start}}^{t_{end}} c(t) \leq c_{min}$$

is satisfied, wherein c(t) denotes the corresponding data values for the amount of carbohydrates from meal intakes at a given time, i.e. denotes a time-dependent carbohydrates input signal, $\Delta y_{min}$ denotes a threshold for a minimum rise in glucose levels/blood glucose levels and wherein $\dot{y}_{min}$ denotes a rate-of-change threshold for the change in glucose levels/blood glucose levels.

If said condition is satisfied, then the time interval $[t_{min}, t_{max}]$, 212, can be considered an invalid rise in glucose levels/blood glucose (BG) levels and data or data segments associated with that invalid rise can be marked as suspicious and can be removed from the first medical data set.

Identifying such an exemplary invalid rise in glucose levels/blood glucose (BG) levels is an example for identifying a predetermined time-dependent data pattern so that data associated to said identified time-dependent data pattern can be removed from first medical data set.

Figure 3:
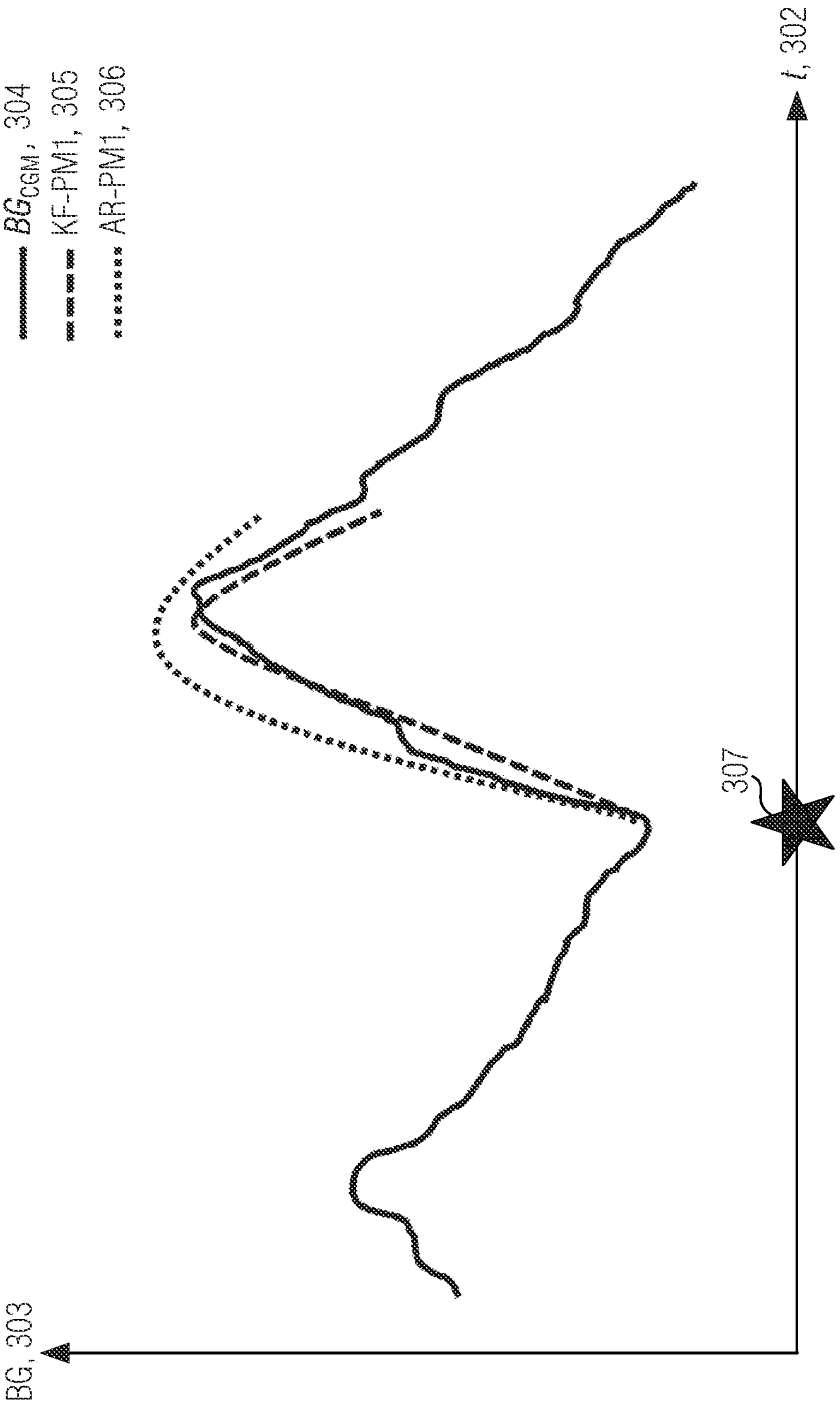
FIG. 3 is an exemplary prediction of postprandial blood glucose levels.

FIG. 3 schematically exemplary shows glucose data/blood glucose data $BG_{CGM}$ (t), 304 of a patient, wherein the data may have been retrieved from a continuous glucose monitoring system.

The shown glucose data/blood glucose data, 304, may be glucose data/blood glucose data from an exemplary second medical data set, i.e., glucose data/blood glucose data that was extracted from a first medical data set according to at least one of the steps, rules or criteria described above.

Analogous to the previous figure, the reference numeral 303 marks the ordinate axis of exemplary blood glucose values, BG, and the reference numeral 302 marks the abscissa axis of exemplary time t.

The star symbol marks an event, 307, on the time line, such as a meal intake and/or an intake of medication, such as a bolus insulin intake.

For example, the event 307 may represent a breakfast meal event of the patient. Furthermore, there are shown two prediction trajectories for the prediction of postprandial blood glucose levels from two different blood glucose level prediction models based on the exemplary second medical data set.

Therein, the reference numeral 305 denotes a prediction of postprandial blood glucose levels based on providing the second medical data set to a blood glucose level prediction model based on the Kirchsteiger model with applied Kalman filter, i.e., a KF-PM1 model and the reference numeral 306 denotes a prediction of postprandial blood glucose levels based on providing the second medical data set to a blood glucose level prediction model based on the Kirchsteiger model in combination with an autoregressive model, i.e., an AR-PM1 model.

As exemplarily described above, the second medical data set can be fed to a blood glucose level prediction model, whose model parameters can be optimized, e.g., by minimizing a cost function, to derive the best-fit model parameters that best fit the data and that allow a prediction of future blood glucose levels of the patient.

While this invention has been described as having an exemplary design, the present invention may be further modified within the spirit and scope of this disclosure. This application is therefore intended to cover any variations, uses, or adaptations of the invention using its general principles.

What is claimed is:

1. A method for predicting blood glucose levels comprising:

receiving a first medical data set of a patient covering a time range, the first medical data set comprising glucose data and other medical data of the patient;

extracting a second medical data set from the first medical data set, wherein the second medical data set is a subset of the first medical data set and wherein the extracting comprises at least one of:

a) identifying duplicates in the first medical data set and removing identified duplicates, b) identifying at least one predetermined time-dependent data pattern and removing data associated with the identified time-dependent data pattern; and c) identifying data values that differ from predetermined expected data values by more than a predetermined amount by checking whether a recorded bolus insulin amount differs from an expected bolus insulin amount by more than a predetermined amount and removing data associated with the identified data values;

providing the extracted second medical data set as input to a blood glucose level prediction model; and predicting future blood glucose levels of the patient using the output of the blood glucose level prediction model based on the second medical data set.

2. The method according to claim 1, wherein the other medical data of the patient comprises at least one of the following: amount of carbohydrates from meal intakes, other data on meal intakes, data on insulin injections, other data on medication, and/or other analyte data.

3. The method according to claim 1, wherein the method comprises identifying duplicates in the first medical data set based on checking whether the duplicates lie within less than a predetermined time interval and removing the identified duplicates.

4. The method according to claim 1, wherein the method comprises identifying data values that lie above a predefined maximum threshold data value based on a value for the predefined maximum threshold data value which is derived from statistical analysis of previously recorded medical data sets of the patient and removing data associated with the identified data values.

5. The method according to claim 1, wherein providing the extracted second medical data set as input to a blood glucose level prediction model comprises identifying in the second medical data set at least one data segment, wherein the at least one data segment is a subset of a plurality of data points of the extracted second medical data set that covers at least a minimum time range.

6. The method according to claim 1, wherein the method comprises identifying data values that differ from predetermined expected data values by more than a predetermined amount by checking whether a recorded bolus insulin amount differs from an expected bolus insulin amount by more than a predetermined amount and removing data associated with the identified data values.

7. The method according to claim 1, wherein the method comprises identifying at least one predetermined time-dependent data pattern and removing data associated to said identified time-dependent data pattern by detecting an invalid rise in glucose levels.

8. The method according to claim 1, wherein providing the extracted second medical data set as input to a blood glucose level prediction model comprises providing the extracted second medical data set as a training data set to a blood glucose level prediction model algorithm and training the blood glucose level prediction model algorithm with the extracted second medical data set.

9. The method according to claim 8, wherein the blood glucose level prediction model is based on the Kirchsteiger model.

10. The method according to claim 1, wherein an obtained prediction of future blood glucose levels is displayed to a patient and, based on the obtained prediction of future blood glucose levels, a recommended dosage of insulin to be administered is displayed to the patient and the recommended dosage of insulin is automatically administered via automatic control of an insulin pump to the patient.

11. A computing system for performing the method according to claim 1, the computing system comprising:

a computer memory;

one or more processors;

a display; and wherein the computing system is configured to receive the first medical data set of the patient and the computer memory comprises computer-executable instructions which, when executed by the one or more processors, cause the one or more processors to perform the method according to claim 1 for predicting blood glucose levels.

12. The computing system according to claim 11, wherein the computing system is one of the following types: a computer server, a personal computer, a smartphone, a tablet, a laptop or other mobile computing system.

13. A glucose monitoring system for performing the method according to claim 1, the glucose monitoring system comprising:

a sensor for obtaining glucose data of the patient;

a computer memory, one or more processors, and a display; and wherein the computer memory comprises computer-executable instructions which, when executed by the one or more processors, cause the one or more processors to perform the method according to claim 1 for predicting blood glucose levels.

14. The glucose monitoring system according to claim 13, further comprising an insulin pump and wherein the glucose monitoring system is further configured to control the insulin pump including controlling the dosage of insulin that is administered by the insulin pump, and wherein the glucose monitoring system is configured to determine a recommended dosage of insulin to be administered based on an obtained prediction of future blood glucose levels.

15. A computer-readable storage medium for storing computer-executable instructions that, when executed by a computer system, performs the method according to claim 1 for predicting blood glucose levels.

16. The method according to claim 1, wherein the method comprises identifying duplicates in the first medical data set and removing identified duplicates.

17. The method according to claim 1, wherein the method comprises identifying at least one predetermined time-dependent data pattern and removing data associated with the identified time-dependent data pattern.

18. A method for predicting blood glucose levels comprising:

receiving a first medical data set of a patient covering a time range, the first medical data set comprising glucose data and other medical data of the patient;

extracting a second medical data set from the first medical data set, wherein the second medical data set is a subset of the first medical data set and wherein the extracting comprises:

identifying data values that lie above a predefined maximum threshold data value based on a value for the predefined maximum threshold data value which is derived from statistical analysis of previously recorded medical data sets of the patient and removing data associated with the identified data values, wherein the predefined maximum threshold data value is based on determining the interquartile range above the 75% quartile of all available data values of a specific data type;

providing the extracted second medical data set as input to a blood glucose level prediction model; and predicting future blood glucose levels of the patient using the output of the blood glucose level prediction model based on the second medical data set.

* * * * *